(12) United States Patent
Bauer et al.

(10) Patent No.: US 9,671,340 B2
(45) Date of Patent: Jun. 6, 2017

(54) MEASUREMENT METHOD FOR DETERMINING AN ORGAN FUNCTION

(75) Inventors: Michael Bauer, Jena (DE); Falk A. Gonnert, Jena (DE); Peter Recknagel, Albrechts (DE)

(73) Assignee: SMARTDYELIVERY GMBH, Jena (DE)

( * ) Notice: Subject to any disclaimer, the term of this patent is extended or adjusted under 35 U.S.C. 154(b) by 336 days.

(21) Appl. No.: 13/813,391

(22) PCT Filed: Jul. 30, 2010

(86) PCT No.: PCT/EP2010/061138
§ 371 (c)(1),
(2), (4) Date: May 24, 2013

(87) PCT Pub. No.: WO2012/013247
PCT Pub. Date: Feb. 2, 2012

(65) Prior Publication Data
US 2013/0234044 A1    Sep. 12, 2013

(51) Int. Cl.
*G01N 21/64*    (2006.01)
*A61K 49/10*    (2006.01)
(Continued)

(52) U.S. Cl.
CPC .......... *G01N 21/64* (2013.01); *A61B 5/0071* (2013.01); *A61K 49/0032* (2013.01); *A61K 49/0034* (2013.01)

(58) Field of Classification Search
CPC .. G01N 21/64; A61B 5/0071; A61K 49/0032; A61K 49/0034
See application file for complete search history.

(56) References Cited

U.S. PATENT DOCUMENTS

| 4,350,674 A | 9/1982 | Molter et al. |
| 5,154,176 A | 10/1992 | Kanda |

(Continued)

FOREIGN PATENT DOCUMENTS

| DE | 3016818 A1 | 2/1982 |
| DE | 4130931 C2 | 5/1994 |

(Continued)

OTHER PUBLICATIONS

Bauhofer, A. et al., "Dependence of Positive Effects of Granulocyte Colony-stimulating Factor on the Antibiotic Regimen: Evaluation in Rats with Polymicrobial Peritonitis," *World J. Surg.*, vol. 28, pp. 834-844 (2004).

(Continued)

*Primary Examiner* — David Porta
*Assistant Examiner* — Jeremy S Valentiner
(74) *Attorney, Agent, or Firm* — McDonnell Boehnen Hulbert & Berghoff LLP (57) ABSTRACT

The invention relates to a method for acquiring data in order to determine organ function, in particular the liver or kidney function, comprising one or more polymethine fluorescent dyes having a fluorescence emission maximum, measured in ethanol, of less than or equal to 820 nm, and to the use of dyes as markers for acquiring data in order to determine the organ function. The invention further relates to a kit for determining an organ function with a marker dye, and to a device for acquiring data in the method.

28 Claims, 7 Drawing Sheets

(51) Int. Cl.
*A61B 5/00* (2006.01)
*A61K 49/00* (2006.01)

(56) References Cited

U.S. PATENT DOCUMENTS

| | | | |
|---|---|---|---|
| 5,321,130 A * | 6/1994 | Yue et al. | 536/23.1 |
| 5,687,726 A | 11/1997 | Hoeft | |
| 6,280,703 B1 * | 8/2001 | Combs | A61B 5/0071 424/1.11 |
| 6,403,625 B1 | 6/2002 | Nagao | |
| 6,853,857 B2 | 2/2005 | Pfeiffer et al. | |
| 2001/0055567 A1 * | 12/2001 | Licha et al. | 424/9.6 |
| 2004/0162423 A1 * | 8/2004 | Czerney et al. | 536/46 |
| 2004/0213740 A1 * | 10/2004 | Achilefu | C09B 23/02 424/9.6 |
| 2009/0004115 A1 | 1/2009 | Agdeppa et al. | |
| 2009/0200167 A1 * | 8/2009 | Kratzmeier et al. | 204/453 |
| 2009/0236541 A1 | 9/2009 | Lomnes et al. | |
| 2009/0285761 A1 * | 11/2009 | Wang | A61B 5/0071 424/9.6 |
| 2010/0080758 A1 * | 4/2010 | Draney et al. | 424/9.6 |
| 2010/0196282 A1 * | 8/2010 | Nairne et al. | 424/9.6 |
| 2011/0168915 A1 * | 7/2011 | Yajima et al. | 250/459.1 |

FOREIGN PATENT DOCUMENTS

| | | |
|---|---|---|
| DE | 68921947 T2 | 7/1995 |
| DE | 10120980 A1 | 11/2002 |
| DE | 69921151 T2 | 6/2005 |
| DE | 10 2005 044531 A1 | 3/2007 |
| EP | 0019790 A2 | 12/1980 |
| EP | 0399482 B1 | 1/1995 |
| EP | 1254630 A2 | 11/2002 |
| JP | 2009-526212 | 7/2009 |
| WO | WO 02/075320 A2 | 9/2002 |
| WO | WO 2007/090468 A1 | 8/2007 |
| WO | 2009/016081 | 2/2009 |
| WO | WO 2009/016181 A2 | 2/2009 |

OTHER PUBLICATIONS

Bauhofer. A. et al., Granulocyte Colony-stimulating Factor Prophylaxis Improves Survival and Inflammation in a Two-hit Model of Hemorrhage and Sepsis, Crit. Care Med.. vol. 34, No. 3. pp. 778-784 (2006).).

English language abstract of DE 10 2005 044531 A1 (1 page).
English language abstract of EP 0039388 A2, corresponding to DE 3016818 A1 (1 page).
International Search Report for PCT/EP2010/061138 (published as WO 2012/013247 A1), dated Apr. 15, 2011 (6 pages).
Lisy, M.R. et al., "Diagnosis of peritonitis using near-infrared optical imaging of in vivo labeled monocytes-macrophages," *J. Biomed. Opt.. SPIE—Int'l Soc. Opt. Eng.*, vol. 11, No. 6, pp. 064014-1 to 064014-9 (2006).
Lorenz, W. et al., "Granulocyte Colony-stimulating Factor Prophylaxis Before Operation Protects Against Lethal Consequences of Postoperative Peritonitis," Surgery, vol. 116, No. 5, pp. 925-934 (1994), Abstract (1 page).
Pola. R. et al "HPMA-copolymer conjugates targeted to tumor endothelium using synthetic oligopeptides." *J. Drug Targeting*, vol. 17, No. 10, pp. 763-776 (2009).
Sakka, S.G. et al., "Prognostic Value of the Indocyanine Green Plasma Disappearance Rate in Critically Ill Patients," *Chest.* vol. 122, No. 5, pp. 1715-1720 (2002).
Dyomics GmbH Catalogue, "Fluorescent Dyes for Bioanalytical and Hightech Applications," pp. 1-85, Oct. 1, 2007.
Van Griensven, M. et al., "Dehydroepiandrosterone (DHEA) Modulates the Activity and the Expression of Lymphocyte Subpopulations Induced by Cecal Ligation and Puncture," *Shock*, vol. 18, No. 5, pp. 445-449 (2002).
Vollmar, B. et al., "High-resolution Microscopic Determination of Hepatic NADH Fluorescence for in Vivo Monitoring of Tissue Oxygenation During Hemorrhagic Shock and Resuscitation," *Microvascular Research*, vol. 54, pp. 164-173 (1997).
Li, et al. "Near infrared fluorescence imaging and spectrum of indocyanine green for laparoscopy diagnosis in gastric cancer," Chinese Optics Letter, col. 10(Suppl.): S21003, Dec. 30, 2012.
Kotake, et al., "The Relationship between postoperative Hyperbilirubinemia and Indocyanine Green clearance after esophagectomy," ICU and CCU, 2004, vol. 28, No. 6, pp. 437-442. Translation of abstract.
Yates, et al., "The Plasma Clearance of Indocyanine Green in Rats With Acute Renal Failure: Effect of Dose and Route of Administration," Biochem. Pharmacol., Oct. 1983, vol. 32, No. 20, pp. 3109-3114.
Bowmer, et al., "The Effect of Acute Renal Failure on the Pharmacokinetics of Indocyanine Green in the Rat," Biochem. Pharmacol., Aug. 1982, vol. 31, No. 15, pp. 2531-2538.

* cited by examiner

MEASUREMENT METHOD FOR DETERMINING AN ORGAN FUNCTION

This application is a national phase application based on International Patent Application No. PCT/EP2010/061138 filed on Jul. 30, 2010, the entire disclosure of which is incorporated herein by reference.

The invention relates to a method for acquiring data in order to determine an organ function, in particular the liver or kidney function, comprising one or more polymethine fluorescence dyes having a fluorescence emission maximum, measured in ethanol, of less than or equal to 820 nm, and to the use of the dyes as markers for acquiring data in order to determine the organ function. The invention also relates to a kit for determining an organ function with a marker dye, and to a device for acquiring data in the method.

There is an increasing need for accurate measurement methods for quantitatively determining the functional capability of an organ, in particular in the case of organ disorders or after transplants. The focus is directed in this case to the liver and kidneys in particular.

Due to its function in intermediary metabolism, but also as an immune organ, the liver plays a central role for the progression and prognosis of critically ill patients. Cell destruction is traditionally evaluated in plasma ("static" tests) on the basis of the release of more or less specific hepatocellular enzymes (for example (ASAT, ALAT, GLDH, etc.).

The leakage of enzymes from the liver in patients suffering from chronic hepatitis or sclerosis decreases however. In addition, fluctuations or high values may also be obtained from an individual if, at the time of the test, the liver function has already recovered from the disorder, since a specific period of time must pass before the leaked enzymes disappear from the blood. Quantitative determinations of the enzymes as test methods for evaluating the current degree of disturbance to the liver function therefore are not usually sufficient.

Bilirubin is traditionally the most commonly used indicator for hepatic dysfunction. Similarly to the other static tests, this indicator can only provide an indirect indication of hepatic function however.

By contrast, dynamic liver tests, such as indocyanine green PDR (plasma disappearance rate), provide more direct details regarding the actual functional state of the liver at the time of examination.

The dynamic tests can provide key partial functions of the hepatocytes, such as the intermediary metabolism of amino acids and proteins, urea biosynthesis, gluconeogenesis, metabolism of xenobiotics or conjugation and excretion capacities, which can be quantified by administration of specific substrates within the scope of the test methods.

Diagnostic agents for liver function are described in European patent specification EP 0 911 040. In this case $^{13}CO_2$-labelled atoms are used via a $^{13}CO_2$ breath test in order to determine the liver function. A similar method is also presented in WO 02/075320 A2.

These tests require the administration of labelled (for example radioactive) traces or substrates however, and are only available with difficulty in the clinical routine, or are unavailable, due to the high logistical cost or the special laboratory methods necessary.

Further marker substances, which can be measured in urine or blood plasma, are 2,4,7-triamino-6-phenylpteridine, as described in DE 301 6818 A1 or pentafluoroacetanilidoiminodiacetate (see EP 0 019 790).

The dye idocyanine green (ICG) can be used to determine perfusion distribution (see DE 10 2005 044 531 A1) or blood volume (see DE 41 30 931 C2). ICG has also been used for a relatively long period of time for the examination of liver function (see ICG-PDR in DE 689 21 947 T2); pulse detection devices have also been used of late (EP 0 399 482 B1).

In recent years, the detection of the indocyanine green plasma disappearance rate (ICG-PDR$_{ICG}$) for evaluating liver function with acute or chronic diseases and after liver transplant has become established as a supplementary measurement method due to practicability and lower time expenditure compared to bedside tests in daily clinical practice (Pulsion Medical Systems AG; DE 101 20 980 A1).

Similarly to any measurement method based on the clearance of a tracer, PDR$_{ICG}$ is dependent on the efficiency of the elimination (hepatocellular performance) and on perfusion.

Indocyanine green (ICG) is an anionic dye with an absorption maximum at a wavelength of approximately 805 nm, which has negligible toxicity at clinically conventional dose (see DE 699 21 151 T2). According to the current state of knowledge, ICG is neither metabolised nor eliminated extrahepatically and is not subject to enterohepatic circulation. Following intravenous injection (0.1-0.5 mg/kg KG), ICG is fully bonded to plasma proteins within a short period of time and appears unconjugated in the bile after approximately 8 min. Hepatic uptake and elimination of ICG are passive and active processes respectively, which depend on cardiac output, sinusoidal perfusion, membrane transport and secretory performance of the liver. In the meantime, the measurement can be taken non-invasively by transcutaneous determination of the PDR$_{ICG}$ by means of pulse dye-densitometry.

Various clinical examinations of different patient groups have shown that this method can detect hepatocellular dysfunction even earlier, and in addition correlates well with the survival rate and has considerable advantages as a prognostic marker compared to the conventional static laboratory parameters.

The transport of ICG in the bile includes at least three steps: the uptake into the hepatocytes through the sinusoidal membrane, the passage through the hepatocytes, and the excretion via the canalicular membrane. These transport steps have only been characterised on the basis of kinetic studies however. To date, there is little data providing information regarding the ratio of PDR$_{ICG}$ and biliary ICG secretion under pathophysiological conditions such as sepsis, shock or endotoxemia. A current study examined the ratio of PDR$_{ICG}$ and biliary ICG excretion with endotoxemia in pigs. Whereas the PDR$_{ICG}$ was practically unchanged, even after 12 hours of endotoxemia, there was still a significant decrease in biliary ICG secretion and in the cumulative bile flow, without the need to record any substantial changes to liver perfusion or oxygen consumption of the liver with hyperdynamic circulation on the whole.

ICG is taken up from the liver sinusoids through the basolateral (sinusoidal) plasma membrane of the hepatocyte. By contrast, ICG is excreted via the apical (canalicular) membrane—a highly energy-dependant transport mechanism, which is extremely sensitive to endotoxin. ICG could thus indeed be taken up into the hepatocytes under specific pathophysiological conditions, such as sepsis, but not eliminated again via the bile, and therefore the determination of PDR$_{ICG}$ for therapy control and prognosis estimation could be unreliable.

The total conversion of ICG is composed of two components: the uptake into the hepatocytes from the blood and the transport of ICG from the liver cells into the bile excretion. The first step is measured primarily by conventional PDR measurements. These two steps are decoupled however in the case of an accumulation of ICG in the hepatocytes and therefore are independent of one another. The overall organ function therefore no longer correlates linearly with the measured PDR because the decrease in the blood is attributed predominately to the first step and no longer constitutes a measure for the excretion into the bile fluid.

If the prehepatic and posthepatic plasma concentrations are not determined, and merely the systemic $PDR_{ICG}$ is measured, both influencing variables (hepatocellular fractional clearance vs. liver blood flow) naturally cannot be discriminated.

In the clinical assessment of excretory kidney function, glomerular filtration is the most significant factor. The gold standard for measuring the glomerular filtration rate (GFR) is inulin clearance, which is methodically too complex for routine use however. In the clinical routine, creatinine clearance can be determined with good approximation as a measure for the GFR. However, this is subject to the disturbances of creatinine determination and is also defective due to errors during the urine collection period. Since creatinine is also secreted via tubular secretion with highly limited GFR, the "true" GFR can also be overestimated by up to 100%. Methods for continuously observing the GFR within the scope of a monitoring process, as is possible for haemodynamic and respiratory parameters, only exist experimentally.

Generally, the object of the present invention is therefore to provide an improved method for determining an organ function, particularly of the liver or kidneys, which avoids the above-described problems.

In particular, the object of the present invention is to provide a method that allows a clinical estimation of the intact hepatocyte mass taking part in the blood flow, that is to say a good estimation of the liver performance and its therapeutic effect.

This method will provide in particular an accurate diagnosis for prognosis in the state of the hepatic dysfunction of the liver due to sepsis or other disorders.

A further object of the invention is to enable improved imaging and a more accurately quantifiable measurement of the marker substances used.

A method, a kit and a device will also be provided, which similarly solve the above-described problems and have advantages.

The above-described problems can surprisingly be solved by the inventive uses, methods, kits and devices described hereinafter.

In particular, the present invention relates to the use of one or more polymethine fluorescence dyes having a fluorescence emission maximum, measured in ethanol, of less than or equal to 820 nm as markers for acquiring data in order to determine an organ function.

As described above, the use of long-wave-emitting polymethine fluorescence dyes for organ diagnostics is already known, and therefore also of ICG for example. Polymethine dyes are conjugated polyenes, in which an electron acceptor is linked to the electron donor via an odd-numbered chain of methine groups.

It was then found that fluorescence dyes that emit below 820 nm lead to improved imaging in fluorescence detection. It is thus possible to establish more accurate details regarding the dye concentrations in blood serum, in other liquid media, or in the organ tissues of the body, for example when determining organ perfusion. Improved resolution in the conventional imaging methods is advantageous in particular for imaging methods or intravital microscopy.

In addition, the dyes emitting with shorter wavelengths can be used in combination with other dyes that are already known, such as ICG, since the emission wavelength ranges can be separated by various filters (for example beam splitters) and can be detected simultaneously or consecutively via a plurality of detection channels.

The dye ICG has 9 carbon atoms and 7 methine groups between the donor and the acceptor (nitrogen in each case). The dyes according to the invention preferably have less than 9 carbon atoms between the donor the acceptor of the conjugated chromophore chain of the fluorescence dye, more preferably seven or five carbon atoms. The chromophore chain most preferably has 7, 5 or 3 methine groups.

The invention also comprises a method for acquiring data in order to determine an organ function, comprising the following steps:
a) radiative excitation of one or more polymethine fluorescence dyes having a fluorescence emission maximum, measured in ethanol, of less than or equal to 820 nm as markers in blood, in a tissue or organ and/or in bile or urine, by means of a radiation source,
b) detection of the fluorescence emission of the one or more polymethine dyes by means of a detection device,
c) acquisition of the data of the measured fluorescence intensity by means of a data acquisition device.

The dyes used allow a more accurate representation of the measured organ function. In addition, they have a lesser tendency for accumulation in the organ tissue.

They therefore not only demonstrate the perfusion movement into the organ, but also better reproduce the actual excretion performance of the organ. The above method is therefore suitable in particular for determining measured values and parameters that can be used for organ function diagnostics.

A laser diode can be used as a preferred excitation source for the radiative excitation (irradiation with light). In order to prevent fading of the dye, the power of the source is preferably less than or equal to 1 $mW/cm^2$ in some imaging methods.

In step c) the data are preferably measured as a function of time. A graph showing fluorescence over time can be derived therefrom.

The measurement of fluorescence in blood plasma is particularly advantageous. The plasma disappearance rate (PDR) of the dye can thus be determined. The clearance function of the dye can be determined from the blood or the organ tissue.

It is favourable that the liver function is then detected "as a whole", since the excretory performance can also be assessed.

The subsequent storage of the data of the measured fluorescence intensity function by means of a data storage device is also preferred.

The processing of the data and/or output of the data at a data output device, for example a display, a printout or a storage medium, is also favourable.

The acquired data are then preferably compared with standard values. In a further step, a (significant) deviation from the standard values can then be established. Lastly, it is then optionally also possible to establish a diagnosis and/or association of the data record with a pathological finding on the basis of this analysis step with the aid of an evaluation programme or with the experience of a trained neural network.

In preferred embodiments of the method, the dye may lastly be administered in a first step. More preferably, one or more polymethine fluorescence dyes are administered by intravenous injection into the bloodstream. Alternatively, the dye can be administered via an existing catheter, whereby there is no need to subject the body to an additional intervention. The administration is preferably carried out at a point that is located no further than 50 cm from the vascular area or organ to be examined.

The dose of the dye varies with the body mass and the requirements of the measurement detection. Typically, 0.05 to 10 mg/kg are used per measurement, more preferably 0.1 to 0.5 mg/kg or to 1.25 mg/kg are used per measurement, and most preferably 0.25 mg/kg or 0.45 mg/kg are used per measurement. Significantly higher values are not recommended, since the cytotoxicity, which is low per se, may rise in this case. It can be seen in FIG. 10 that, in the comparison of cytotoxicity between ICG and DY635, the latter dye has very low cytotoxicity and does not appear to be any less viable than ICG.

In an advantageous embodiment, the fluorescence detection takes place in vitro in the above use or method. In this case, the measured values can be determined in a laboratory once a sample has been taken.

The fluorescence detection is preferably carried out in the blood, tissue or organ and/or the bile or urine of an animal with the use or method according to the invention; this animal is preferably a mammal, rodent or homosapien.

The invention also comprises a kit for determining an organ function with a marker dye, comprising:
one or more polymethine fluorescence dyes having a fluorescence emission maximum, measured in ethanol, of less than or equal to 820 nm, which is/are present in a physiologically compatible administration form,
a fluorescence detection device,
and a fluorescence data acquisition device.

This kit has the advantage of providing the means for efficient organ function diagnostics in a compact manner.

The kit according to the invention typically comprises enough storage for one to two or more doses of the dye. Multi-dosing units can contain up to 100, 200 or 500 doses. In this case, the further components of the kit are reusable.

The kit is preferably used to measure the PDR. In this case, the detector is expediently a disposable sensor for taking a measurement at the ear lobe.

In a preferred development of the invention, the kit also comprises one or more of the following elements: an administration device (preferably an injection needle or a central or peripheral catheter), a data storage device and a data output device.

In a specific embodiment of the invention, one or more polymethine fluorescence dyes are provided in a physiologically compatible and intravenously injectable solution. These can be administered most preferably via an existing catheter so that there is no need to subject the body to any further interventions.

The kit preferably comprises a dosing unit, which can be a vial, in which the dye solutions can be stored. In such a case, the kit comprises portions containing 25 mg of dye in ml of solvent, or preferably 50 mg of dye in 10 ml of solvent, preferably water.

In an alternative embodiment, the kit contains the dye in the form of powder in individual dosing units, and optionally the corresponding amount of solvent so as to produce the physiological solution in situ. This variant has the advantage of improved storage stability of the kit components.

When using the kit, sterile handling is important. The kit preferably includes instructions for use.

The above-described inventive use, method or kit for determining an organ function can then preferably be used in particular if the organ, of which the function is determined, is the liver and/or the kidneys. The used dyes of the invention in particular have the advantage in these organs of better representing the actual organ function because the actual excretion performance of the organ is reproduced more accurately with said dyes.

A use, method or kit according to the invention, wherein the fluorescence emission maximum of the one or more polymethine fluorescence dyes, measured in ethanol, is less than or equal to 810 nm, is particularly preferred.

The fluorescence emission maximum is more preferably less than or equal to 780 nm or 740 nm, most preferably less than or equal to 680 nm. The use of dyes having a fluorescence emission maximum of less than or equal to 550 nm may be suitable for specific methods, in particular in combination with a dye having a fluorescence emission maximum of greater than or equal to 750 nm.

The absorption maximum of the dye is preferably 580 nm to 690 nm. An absorption maximum of 600 nm to 670 nm is particularly preferred.

In order to prevent fading of the dye and therefore distortion of the measurement results, the dye should have a high fading stability. It is likewise sensible to use dyes having a high fluorescence quantum yield, since these have greater luminosity with corresponding excitation.

A preferred embodiment of the invention therefore comprises a use, method or kit, wherein the dye is a benzopyrylium-based hemicyanine or an indodicarbocyanine-chromophore.

The number of carbon atoms between the donor and the acceptor group at the dye is preferably less than or equal to 7. This has the effect that the dye has improved photostability and storage stability. Compared to longer-chained chromophores, such as ICG, the shorter conjugated double-bond chain of the dye with its shorter and less pronounced electron cloud provides fewer attack positions for electrophilic or nucleophilic reagents. This increases the photostability of the dyes according to the invention, which leads to a more accurate collection of measured data in quantitative imaging and fluorescence detection methods.

In particular, the one or more dyes of the invention may be an asymmetrical polymethine having a substituted omega-(benz[b]pyran-4-yliden)alk-1-enyl) unit of general structure 1:

1 with Z as substituted benzoxazole derivative, benzothiazole derivative, 2,3,3-trimethylindolenine derivative, 2,3,3-trimethyl-4,5-benzo-3H-indolenine derivative, 2- and 4-picoline derivative, lepidine derivative, quinaldine derivative and 9-methylacridine derivative of general structure formulas 2A or 2B or 2C wherein
X stands for an element from the group O, S, Se or the structural element N-alkyl or C(alkyl)$_2$,
n stands for the numbers 1, 2 or 3,
$R^1$-$R^{14}$ are the same or different and can be hydrogen, one or more alkyl, or aryl, heteroaryl, or heterocycloaliphatic residues, a hydroxyl group or alkoxy group, an alkyl-substituted or cyclic amine function, and/or can form two ortho residues, for example $R^{10}$ and $R^{11}$, $R^4$ and $R^5$ and/or $R^6$ and $R^5$ together with a further aromatic ring,
at least one of the substituents $R^1$-$R^{14}$ can represent a solubilising or ionisable or ionised substituent, such as cyclodextrin, sugar, SO$_3^-$, PO$_3^{2-}$, COO$^-$, or NR$_3^+$, which determines the hydrophilic properties of these dyes, wherein this substituent can also be bonded to the dye via a spacer group,
and
$R^1$ represents a substituent, which has a quaternary C atom, preferably t-butyl and adamantyl, in the alpha position at the pyran ring.

In advantageous embodiments of the use, method or kit according to the invention, the dyes are provided with substituents in such a way that they are each adapted to different organs. It has thus been found that dyes suitable for the kidneys should not have an excessively low water solubility.

The polymethine fluorescence dyes for determining kidney function are therefore characterised in that the one or more dyes are soluble in water, but are insoluble in DMF or DMSO. These dyes tend to be hydrophilic.

By contrast, the polymethine fluorescence dyes according to the inventive use, method or kit for determining liver function are characterised in that the one or more dyes are soluble in DMF or DMSO and are insoluble in water. These dyes tend to be fat-soluble and hydrophobic.

In particular, the one or more dyes preferably have a neutral charge in physiological solution or are provided charged once at most and/or preferably have at most two solubilising or ionisable or ionised substituents. These developments are particularly suitable for determining liver function.

In other developments of the invention, the one or more dyes are provided in physiological solution charged at least twice and/or preferably have at least three or four solubilising or ionisable or ionised substituents.

The aforementioned solubilising or ionisable or ionised substituents are particularly preferably sulfonic acid groups, carboxylic acid groups or ammonium groups in this case.

It is particularly preferable for the one or more dyes according to the invention to be selected from the group comprising:
DY630, DY631, DY632, DY633, DY634, DY635, DY636, DY647, DY648, DY649, DY650, DY651 and DY652, as well as DY590, DY548, DY495, DY405.

These dyes preferably have an absorption in the red spectral range. Red-absorbing, green-absorbing or blue-absorbing dyes can also be used however.

The dye DY635 is most preferred, that is to say:
1-(5-carboxypentyl)-3,3-dimethyl-2-[3-(11-(2,2-dimethyl-ethyl)-1H,2H,3H,5H,6H,7Hpyrano[2,3-f]pyrido[3,2,1-ij] quinolin-9-yliden)-1-propenyl]-3H-indolium-5-sulfonate
Or
10-tert-butyl-8-{(E)-3-[1-(5-carboxy-pentyl)-3,3-dimethyl-5-sulfo-1,3-dihydro-indol-(2E)-ylidene]-propenyl)-2,3,5,6-tetrahydro-1H,4H-11-oxonia-3a-aza-benzo[delanthracene
as shown below:

DY647 is also preferred, that is to say:
2-{(1E,3E)-5-(3-(3-carboxy-propyl)-1-ethyl-3-methyl-5-sulfo-1,3-dihydro-indol-(2E)-ylidene]-penta-1,3-dienyl)-1-ethyl-3,3-dimethyl-5-sulfo-3H-indolium or DY652, that is to say:
2-tert-butyl-4-{(E)-3-[3-(3-carboxy-propyl)-3-methyl-5-sulfo-1-(3-sulfo-propyl)-1,3-dihydro-indol-(2Z)-ylidene]-propenyl)-5,7,7-trimethyl-8-(3-sulfo-propyl)-7,8-dihydro-1-oxana-8-aza-anthracene
as shown below:

The kidney or liver organ function can be evaluated using these dyes.

As validated liver function markers, these are suitable in particular as parameters for measuring hepatically eliminated substances, in particular in the case of sepsis-associated liver dysfunction. These dyes have a substantially shorter residence time in the hepatocytes. In this case there is thus a closer correlation between the PDR measurement results and the actual excretion in the bile, thus resulting in improved significance in terms of liver function than with ICG-PDR.

By contrast, the dyes suitable for the kidneys can be used for early detection of kidney dysfunction on the basis of a reduced dye clearance.

In this case, the dye DY647, which can be used for kidney function diagnostics due to its hydrophilic properties and the exclusive excretion via the kidneys, is particularly preferred. The measurement of the PDR of this dye constitutes a simple and quick alternative that is unsusceptible to errors for determining creatinine clearance. DY652 is also preferred.

ICG can likewise be modified by hydrophilic substituents, for example by the incorporation of ionisable groups, such that it is suitable for the described kidney function diagnostics.

The simultaneous use of a plurality of dyes is particularly advantageous. The invention thus also comprises the combinations of a kidney function marker with a liver function marker.

These combinations preferably comprise DY635, DY652 and/or DY647, with a mixture of two dyes from DY635, DY652 and/or DY647 being particularly preferable in this case, for example DY635 with DY652 or DY635 with DY647.

The combination of shorter-wave-excitable dyes with longer-wave-excitable dyes is even more advantageous, because these dyes then each emit in different spectral ranges and the fluorescence of the marker can thus be measured separately in different detection channels. Combinations of DY652 with ICG, or DY635 with ICG, or DY548 with DY635 are preferred in this case.

The kidney function and the liver function can therefore be determined simultaneously by means of a single fluorescence measurement, therefore via PDR for example.

The invention further comprises a device for acquiring data with a marker in order to determine liver function or kidney function by measuring the fluorescence of one or more polymethine fluorescence dyes having a fluorescence emission maximum, measured in ethanol, of less than or equal to 800 nm.

The device selectively also preferably comprises one or more of the following units:
an administration device, a radiation source (preferably a laser diode), a detection device (preferably a CCD camera), a data acquisition device (preferably a computer), a data storage device (preferably a computer), a data output device (preferably a display, a printout or a storage medium).

The invention also relates to a use, a method, a kit or a device as described above for monitoring an organ function following a liver or kidney transplant, for diagnosis of critically ill patients in the event of sepsis, in the event of multiple organ failure or for preventative examination.

Lastly, a blood plasma, bile or urine sample for acquiring data in order to determine an organ function comprising one or more polymethine fluorescence dyes having a fluorescence emission maximum, measured in ethanol, of less than or equal to 820 nm as markers will also be described herein in accordance with the invention.

The above blood serum, bile or urine sample preferably comprises one of the dyes according to the invention, as already described herein.

EXAMPLES AND EXPERIMENTS

Male WISTAR rats (12-16 weeks old, body mass 400±50 g; Harlan Laboratories, Horst, Netherlands) were used in this study. All tests were carried out in accordance with the German laws for the protection of animals and with the approval of the regional animal protection commission in Bad Langensalza, Thuringia, Germany. The body temperature was kept constant at 37° during the surgical preparation and the experimental tests, in each case using a warming plate and a heatable specimen stage of the microscope. All preparations were carried out under aseptic conditions.

A special model of polymicrobial sepsis with some modifications was used, which was originally described by Bauhofer (Bauhofer et al., 2004, 2006; Lorenz et al., 2004). With this model the sepsis is induced by peritoneal contamination and infection (PCI).

A standardised human stool inoculum was used for the PCI. Immediately after collection, the stool sample was diluted 1:1 with pre-reduced thioglycolate-bouillion, containing 10% sterile barium sulphate and 10% glycerol, and was then homogenised under anaerobic conditions. Lastly, the stool samples were stored at −80° C. until use. Before the inoculation, the stool samples were diluted 1:4 in 0.9% NaCl. The inoculum was analysed microbiologically in order to establish the number of strains after storage. The rats were instrumented 24 h before the PCI and anaesthetised using Desflurane (Baxter, Munich, Germany) via a facemask. A jugular vein catheter (polyethylene, autoclave-sterilised, OD:1.0 mm, Portex, UK) was used for the fluid replacement and was tunneled subcutaneously as far as the approach to the nape of the neck. The catheter was mounted on a hinge-jointed retaining system, which enabled unrestricted movement in the cage after recovery from the anaesthetic.

In introductory studies, the dose of the inoculum was adapted such that a 100% mortality rate was achieved within 40 h. The animals were assigned randomly to the control group (sham) or the PCI group. With short ether anaesthesia, the inoculum was injected intraperitoneally into the pelvis region using a 21 G cannula. The animals in the control group (sham) received 0.9% NaCl in the same amount. After the procedure, both groups received fluid replacement (10 ml/kg/KG/h, Jonosteril®, Fresenius Kabi GmbH, Germany) as well as food and water ad libitum.

In order to determine the clinical status at a previously determined moment in time for future experiments, the activity was quantified using a points system in accordance with earlier descriptions (Van Griensven et al., 2002). The number of points obtained reflects spontaneous activity as well as the response to exogenous stimuli. The number of points ranged from 1 to 5, wherein 1 represents high activity and the activity decreases continuously to 5, which lastly stands for a lethargic state. The food uptake (g/rat) was also measured at 15 h. After the laparotomy, the peritoneal fluid volume (ml/rat) was measured and the formation of a fibrin film was quantified on the basis of a points-based assessment between 0 (none) to 3 (massive) (see also FIG. 1 in this regard). The distribution of points was carried out by two of the authors independently of one another in a blind assessment. Both observers assessed each rat. The allocation of points for each individual rat was ultimately formed from the average of both values.

In Vivo Assessment of the Hepatic Clearance Function

The plasma disappearance rate (PDR) and the bile excretion of the dyes DY635 (Dyomics, Jena, Germany) and indocyanine green as a comparative experiment (ICG; Pulsion, Munich, Germany) were determined in vivo.

The animals were anaesthetised 15 h after sepsis or induction of the control group. Particularly since ketamine has been found to most closely resemble the conscious state, measured by cardiac output and regional blood flow (Seyde et al. 1984), the rats were anaesthetised using a mixture of ketamine (Ketamin® 50 mg/ml; Deltaselect, Pfullingen, Germany) and Midazolam (Midazolam-ratiopharm® 5 mg/ml; Ratiopharm, Ulm, Germany), which was administered via a jugular vein catheter (polyethylene, sterilised by autoclave, OD: 1.0 mm, Portex UK) in a dose of 40 mg/kg or 4 mg/kg of body weight.

An arterial catheter was used for haemodynamic monitoring. A midline and right subcostal laparotomy was performed and the ductus choledochus was provided with a polyethylene catheter (polyethylene, autoclave-sterilised, OD:1.0 mm, Portex, UK) for the collection of bile via a cannula. The wound was then closed using Mersilene 2-0 (Ethicon, Hamburg, Germany) and the anaesthetisation was maintained.

The dye was administered via a jugular vein catheter. The blood samples and bile samples were taken from the zero point and then every 15 min for a period of 60 min. Blood losses caused by these blood samples were adequately counter balanced by infusions. The haemodynamic monitoring was carried out continuously.

Figure 3:
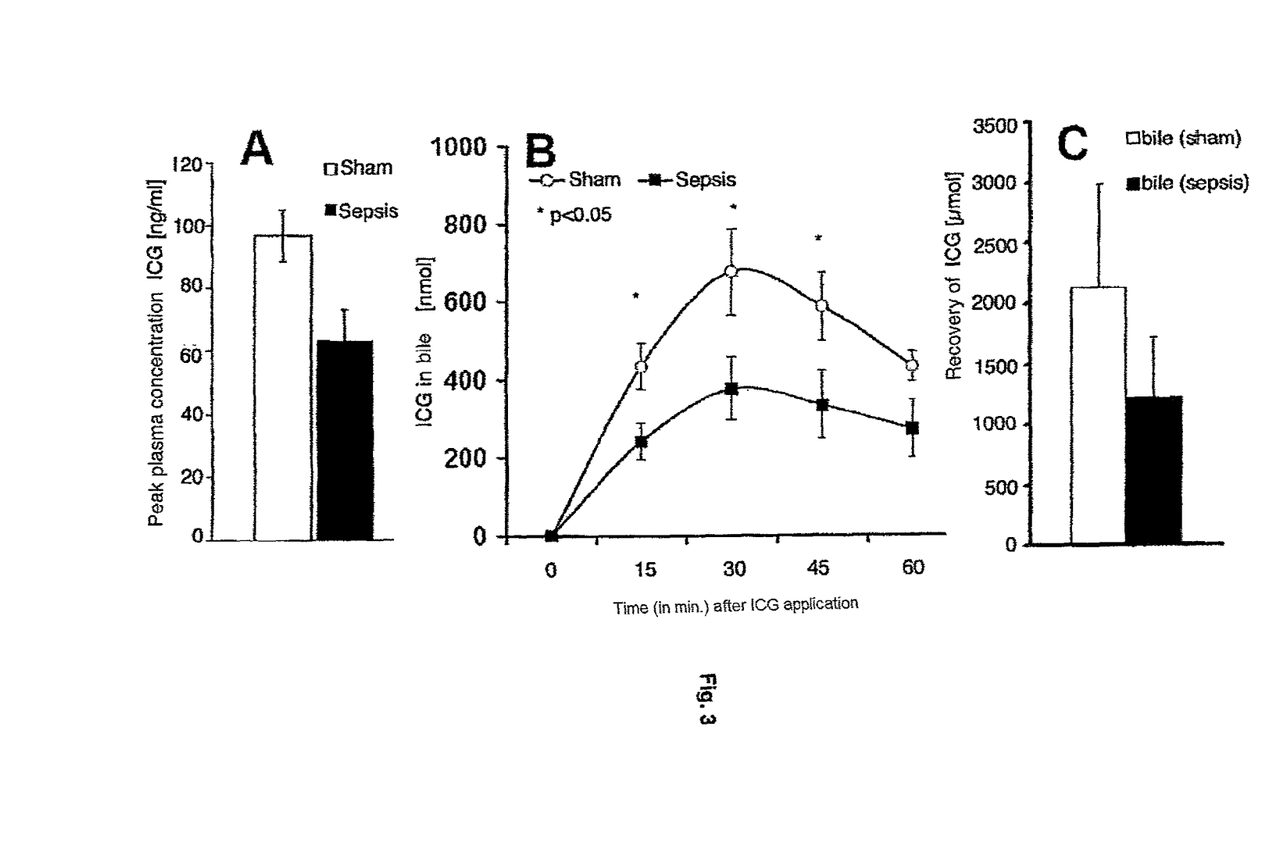
Figure 4:
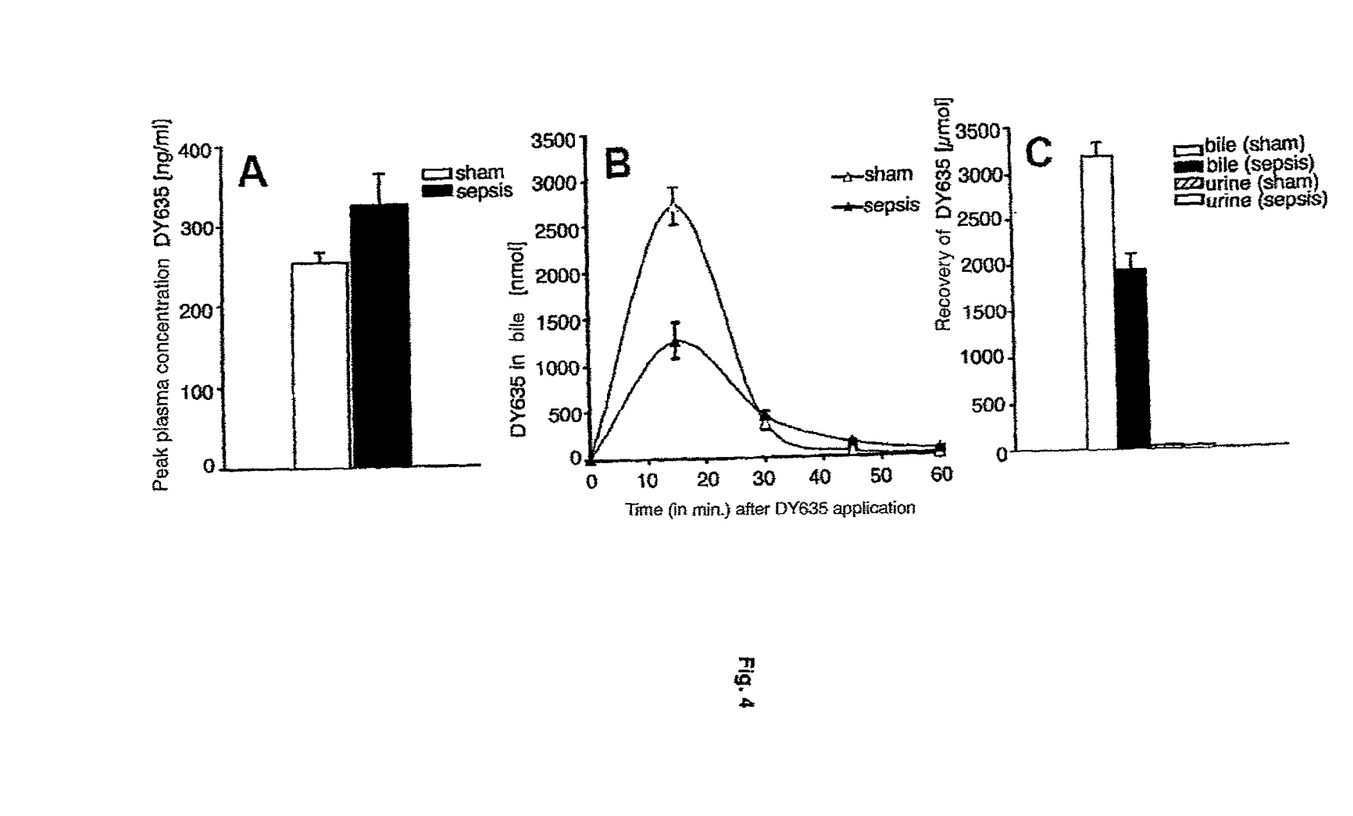
FIG. 4: DY635 kinetics in plasma and bile. (A) shows the plasma concentration of DY635 immediately after application. (B) shows the progression over time of the DY635 concentration in the bile. (C) shows the cumulative amount of DY635 that had collected in the bile within a period of 60 minutes after application.

The results are illustrated in FIGS. 3 and 4.

In Vivo Determination of Hepatocellular and Canalicular Transport

Changes to the hepatocellular uptake and the canalicular elimination were measured 15 h after sepsis or induction of the control group by in vivo imaging of the exclusively hepatocytically eliminated dye indocyanine green (Pulsion, Munich, Germany) and of DY635 using an inverted epiflourescence microscope (AxioObserver® Z1; Zeiss, Jena, Germany), equipped with a computer-controlled, highly-precise scanning platform (Marzhäuser, Wetzlar, Germany).

The surface of the liver was irradiated in epi-arrangement by a 100 W mercury lamp with use of an ×40/0.6 lens, and the liver architecture was visualised by natural autofluorescence of the hepatocellularly reduced pyridine nucleotides (NADH) with use of two filter sets with a 365 nm to 395 nm excitation and 445 nm to 450 nm emission bandpass filter. 775 nm to 805 nm excitation and 845 nm to 855 nm emission bandpass filters were used to image the dye indocyanine green.

All microscope images were imaged on a high-resolution CCD digital video camera (C9100-13; Hammamatsu Photonics, Japan), which was equipped with a PC with Microsoft-Windows®-based software for operation of the microscope, navigation of the scanning stage and image analysis (AxioVision® Rel. 4.6; Zeiss, Jena, Germany).

The animals were anaesthetised using ketamine and Midazolam as above 15 h after sepsis or induction of the control group. A midline and left subcostal laparotomy was performed for definition of the left lobe of the liver. In order to minimise respiratory movements, hepatic ligaments were separated. The intestine was covered with saline-saturated gauze so as to prevent tissue dehydration. Once the animals had been transferred to the microscope stage, the rats were turned onto their left side. The mobilised left lobe of the liver was exposed and the pragmatic surface positioned on a microscope cover glass (#1; Menzel, Braunschweig, Germany) and fixed lightly with Histoacryl (Braun, Melsungen, Germany). An area of 1-1.5 $cm^2$ of the lobe of the liver could thus typically be examined by means of intravital microscopy. In order to prevent the liver from drying out during the intravital microscopy procedure, it was rinsed regularly with warm Ringer's solution) (37°.

In a first step, the hepatocellular NADH autoflourescence was examined in order to establish the mitochondrial oxidation stage (Vollmar et al. 1997). Five randomly selected fields of vision per animal were recorded with use of an ×5 lens and a 365 nm to 395 nm excitation and 445 nm to 450 nm emission bandpass filter. Standard settings were used for all fields of vision for the amplification, exposure time and image enhancement of contrast. The NADH autoflourescence was determined densitometrically and was expressed as average intensity per field of vision (arbitrary units [aU]).

Five 15s video sequences were recorded using an ×20 lens, but with use of the same filter block, in order to determine hepatic microcirculation.

The failure of sinusoidal perfusion was determined on the basis of the number hepatic sinusoids not perfused (measured in percent of the sinusoids intersecting a 100 µm circle). So as to also collect information concerning the type of flow into the perfused sinusoids, the microcirculatory flow index (DeBacker et al. 2007) was determined with some modifications (see FIG. 2). In this case, a video sequence was divided into four quadrants and the predominant flow type (1=slow, 2=normal, 3=quick) was determined in each quadrant by two independent observers.

In order to locate 16 regions (regions of interest: ROI) for the in vivo imagings of the dye, the liver surface was rasterised; 8 pericentral and 8 periportal regions were established and the exact position thereof was determined on the computer-controlled scanning stage using AxioVision® software and stored so that the predefined ROI were accessible during future experiments. The phototoxicity was limited by reducing the light transmission to 20% using a neutral density filter during the identification of the ROI.

Before the indocyanine green or DY635 was added, base line images of the defined ROI were recorded using the AxioVision® multi-channel module (×40/0.6 lens, 365 nm to 395 nm excitation and 445 nm to 450 nm emission bandpass filter and 775 nm to 805 nm excitation and 845 nm to 855 nm emission bandpass filter). The optimal settings for the amplification, exposure time and image enhancement of contrast were established in previous tests. The dye was then administered via a jugular vein catheter and images of all ROI were recorded every 5 min over a period of 35 min (see FIG. 5).

The fluorescence intensity of indocyanine green or DY635, which was distributed in the microcirculatory and hepatic tissue, was quantified densitometrically and was expressed as average intensity per ROI (arbitrary units [aU]).

In Vivo Determination of Kidney Function

Further experiments were carried out to ascertain kidney function using DY652 (data not shown here) and DY647.

Figure 7:
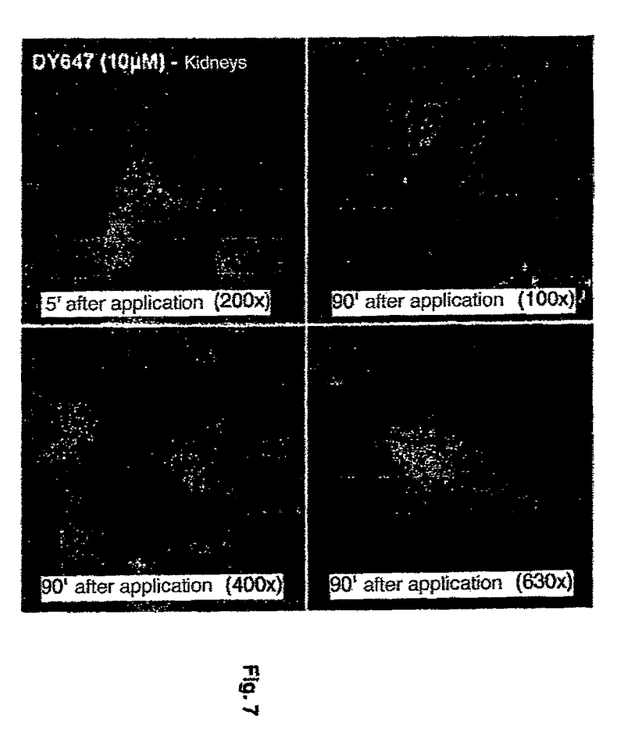
FIG. 7: in vivo imaging of the excretion of DY647 via the kidneys. The dye can be seen in the vascular system of the kidneys 5 minutes after application. After 90 minutes, the dye has left the vascular system and can be seen in the kidney tubules.

The results for DY647 are shown in FIG. 7. The kidney tissue and the widely ramified kidney vascular system can be seen in the recorded images. As can be seen in the recorded images, the dye has left the vascular system and can be seen in the kidney tissue, in this instance in the kidney tubules. After application, the dye was detected in urine.

In Vivo Quantification of Organ Dysfunction During Sepsis

Blood samples for determining organ dysfunction were taken from the retrobulbar plexus of the animals under anaesthetic before the surgical preparation for intravital microscopy.

The following values were then determined by means of automated veterinary haematology and clinically chemical analysers:

Haemoglobin (Hb), haematocrit (Hk), white blood cell count (WBC), platelet count (PLT), aspartate aminotransferase (AST), γ-glutamyltransferase (γGT), bilirubin, albumin, ammonia ($NH_3$) and lactacte dehydrogenase (LDH) (Fuji Dri-Chem 3500i and Poch-100iv-Diff, Sysmex, Leipzig, Germany).

Figure 1:
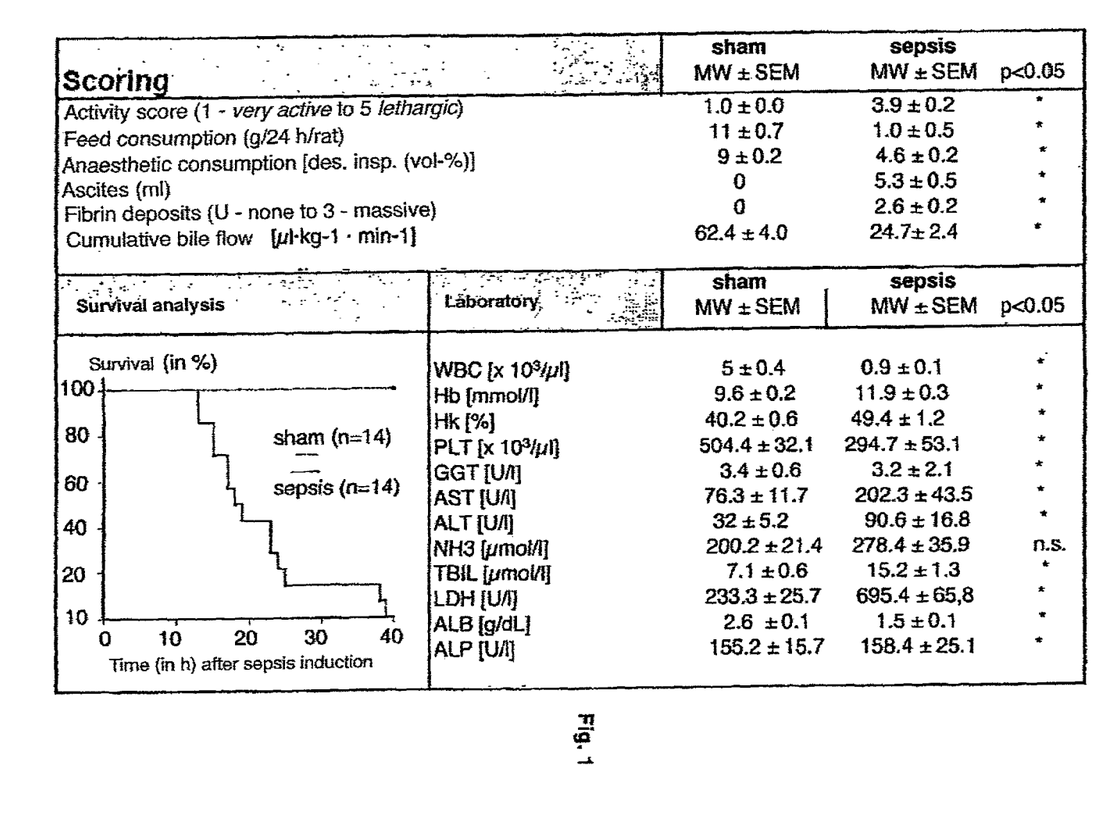

These data are summarised in FIG. 1.

The invention will now be explained in greater detail on the basis of the following figures and results.

FIG. 1: characterisation of the sepsis model used. The survival analysis after sepsis induction is shown. The intervention occurred 15 hours after sepsis induction—mortality was approximately 20% at this point. The animals were clinically assessed before the examination and different laboratory parameters were determined for the assessment of organ dysfunctions.

FIG. 3: ICG kinetics in plasma and bile. (A) shows the plasma concentration of ICG immediately after application. (B) shows the progression over time of the ICG concentration in the bile. (C) shows the cumulative amount of ICG that had collected in the bile within a period of 60 minutes after application.

FIG. 5: in vivo imaging of DY635 and ICG in the liver. (A) shows the relative decrease in fluorescence intensity of both dyes after application. An accumulation of the dye is observed in the septic animals (A, B).

FIG. 6: comparison of the cytotoxicity between ICG and DY635. In each case the survival of cultivated hepatocytes 24 h after addition of different concentration of the dyes is shown (MTT assay).

Comparative studies were carried out on the basis of the known liver function marker ICG.

FIG. 1 characterises the underlying sepsis model. On the whole, the animals were suffering from severe sepsis at the time of examination. One fifth of the animals had already died and the surviving animals were showing considerable signs of disease. The laboratory chemistry also indicated severe hepatic dysfunction.

Figure 2:
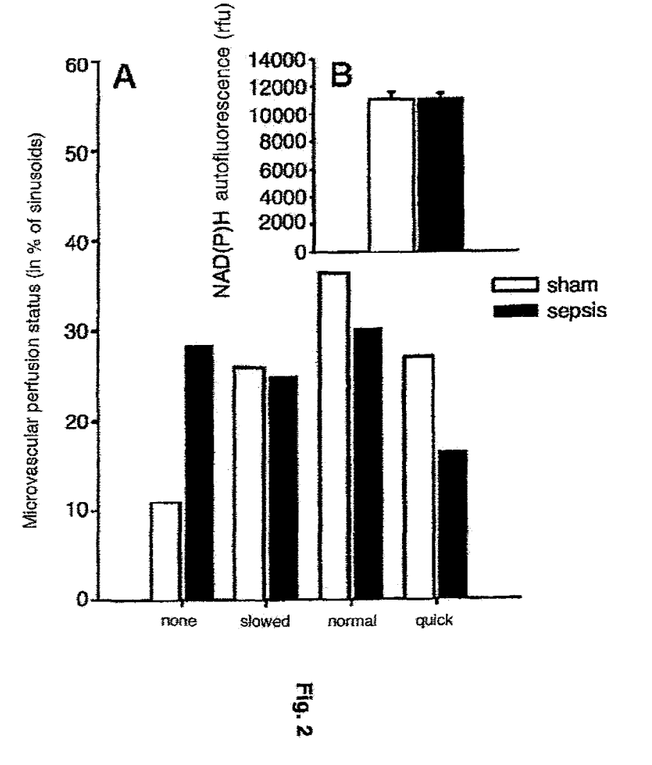
FIG. 2: evaluation of microcirculation and energy status 15 hours after sepsis induction. The energy status was not compromised, microcirculation was moderately restricted.

Microcirculation and energy status were also examined since these also determine hepatocellular transport besides the cellular transport systems. FIG. 2 shows that the energy status in septic animals was not impaired. In terms of microcirculation, only a slight compromise was established in the septic animals. On the whole, fewer sinusoids were perfused in the septic animals. This is insignificant in terms of function however, since practically no dye could be detected any more in the plasma 15 minutes after application of both dyes (data not shown).

FIGS. 3 and 4 each show aspects of the kinetics of the two dyes in serum and bile. Less ICG can be traced in the plasma of the septic animals immediately after application. Uptake therefore is not delayed. The measurement (likewise illustrated) of ICG in the bile shows an initial rise in the concentration, which falls again slowly from 30 min. In this case, it can be seen that the control group has both a sharper rise and also a quicker uptake of the ICG concentration. This can be explained by a greater active excretion via the canalicular membrane into the bile in the control group. After 60 minutes, high ICG values could still be measured. This can be seen in FIG. 3B at the continuous line, which represents the concentration in the bile. The disturbed excretory organ function in the sepsis group is restricted compared to the control group (sham) and this difference can be established on the basis of the ICG dye measurements in the bile. These results therefore confirm the suitability of ICG as a liver function marker, although not in the conventional sense of a measurement of the plasma disappearance rate (PDR-ICG). ICG was used in the setting shown here as a marker for excretory liver function. Numerous scientific works indicate that the canalicular transport systems of the hepatocytes in particular are very sensitive to a pro-inflammatory state and are thus compromised early. Conventional PDR-ICG measurements may therefore show "false-high" PDRs, since there is not necessarily a direct correlation between measured serum fluorescence uptake and excretory liver function. The PDR-ICG measures merely the uptake and storage of the dye in the hepatocytes and cannot provide an indication regarding the actual excretion performance of the liver.

The examinations of ICG kinetics in plasma and bile were carried out similarly for DY635 (FIG. 4). Less DY635 in the plasma was traceable in the healthy animals than in the sick animals immediately after application of DY635. The hepatocellular uptake was thus prolonged. However, the dye was taken up completely into the hepatocytes within 15 min, both in the control group and in the sepsis group (data not shown). After 60 min, the dye also could not be detected in the kidneys or in the urine. The measurement of DY635 in the bile shows that the control group has both a sharper rise and a quicker uptake of the DY635 concentration than the sepsis group. These results therefore confirm the suitability of DY635 as a liver function marker.

In addition, however, the rise and the subsequent fall are also more pronounced than in the comparative tests for ICG. The dye DY635 is thus excreted more quickly canalicularly into the bile fluid.

The difference in bile excretion between the control group and the sepsis group in the case of DY635 is also much more pronounced than for ICG. After 60 min, 60% of the applied DY635 had already been excreted canalicularly in the control animals. By contrast, only 34% had been excreted within the same period in the septic animals. The dye DY635 already accumulates much less considerably in healthy animals than ICG, wherein an accumulation is likewise observed with restricted excretory performance, similarly to ICG.

Figure 6:
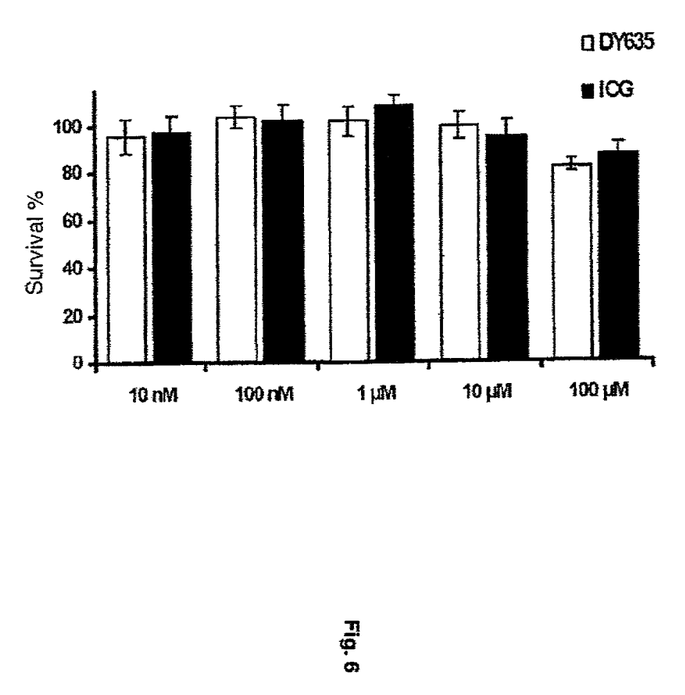

FIG. 6 shows that there is no indication of increased toxicity in the cytotoxassay compared to ICG.

Figure 5:
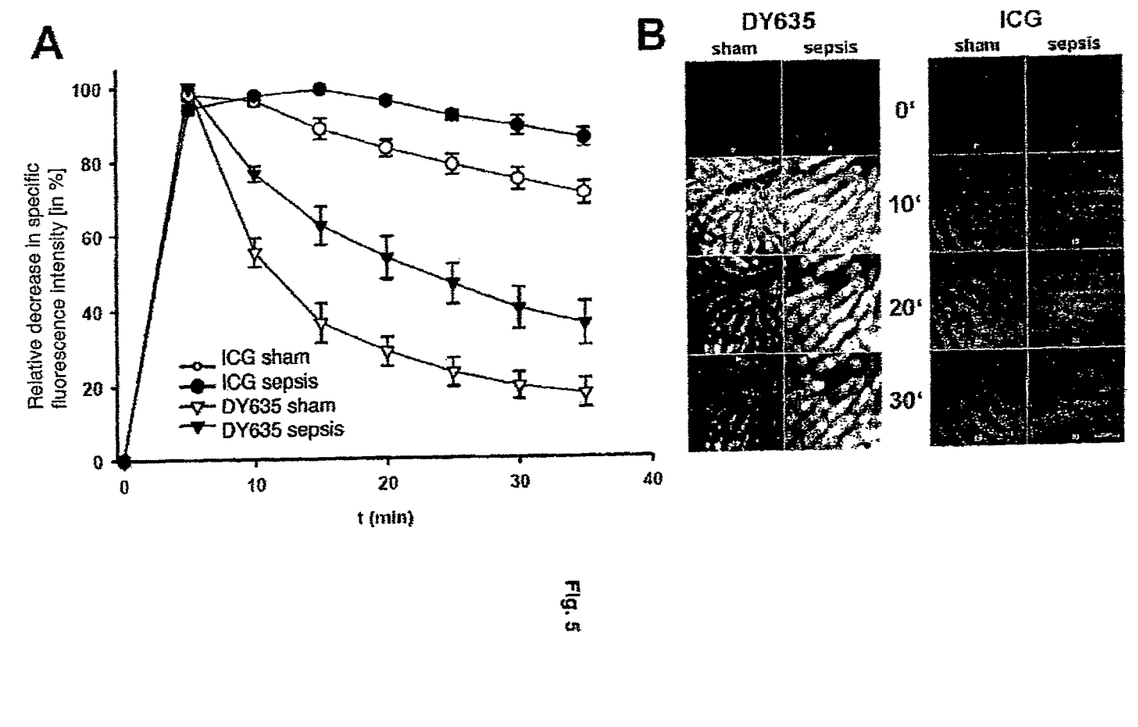

FIG. 5 shows the results of the in vivo imagings for ICG and DY635. The fluorescence of DY635 and ICG was detected by means of intravital microscopy in periportal and perivenous liver areas at intervals after application. In particular, the fluorescence provides information concerning the hepatocellular accumulation of the dyes. In conformity with the concentration determinations of both dyes in the bile, the specific fluorescence intensity and therefore the dye concentration in the organ tissue decreases much more sharply with DY635 than for ICG. The difference between the sepsis group and the control group is also more pronounced than with ICG, in particular in the first minutes after administration. The corresponding images show a much clearer resolution of DY635. In particular, this fact and also the fact that DY635 does not already tend to accumulate in healthy animals make DY635 particularly suitable for in vivo imaging applications.

Within the scope of in vivo measurements of the kidneys, it has been found that the water-soluble dye DY647 is excreted selectively via the kidneys (FIG. 7). Excretion with an underlying dysfunction leads to delayed excretion and therefore to prolonged traceability in the blood. The situation is similar with DY652. The dyes DY652 and DY647 suitable for the kidneys are therefore suitable as kidney function markers in organ diagnostics.

The invention claimed is:

1. A method for determining at least one organ function of a liver or kidney, the method comprising the steps of:
    a) exposing at least one polymethine fluorescence dye in a medium to a radiation source, wherein
        the medium consists of an in vivo bodily fluid and at least one polymethine fluorescence dye without biological targeting moieties dissolved in a suitable solvent, and wherein
        the polymethine fluorescence dye has a fluorescence emission spectrum with a peak maximum of 820 nm or less when measured as a solution consisting of the polymethine fluorescence dye and ethanol;
    b) detecting a fluorescence emission of the polymethine dye with a detection device; and
    c) measuring a fluorescence intensity with a data acquisition device,
        wherein the organ is a liver or kidney.

2. The method according to claim 1, wherein the organ function is a kidney function, and the polymethine fluorescence dye is soluble in water, and insoluble in dimethylformamide (DMF) or dimethyl sulfoxide (DMSO).

3. The method according to claim 1, wherein the organ function is a liver function, and the polymethine fluorescence dye is soluble in dimethylformamide (DMF) or dimethyl sulfoxide (DMSO), and insoluble in water.

4. The method according to claim 1, wherein the polymethine fluorescence dye comprises a benzopyrylium-based hemicyanine dye, an indodicarbocyanine chromophore, or a combination thereof.

5. The method according to claim 4, wherein the polymethine fluorescence dye comprises an asymmetrical polymethine dye having a substituted omega-(benz[b]pyran-4-yliden)alk-1-enyl) unit of general structure 1:

1 wherein
Z is a substituted benzoxazole derivative, a benzothiazole derivative, a 2,3,3-trimethylindolenine derivative, a 2,3,3-trimethyl-4,5-benzo-3H-indolenine derivative, a 2-picoline derivative, a 4-picoline derivative, a lepidine derivative, a quinaldine derivative, or a 9-methylacridine derivative of general formula IIa, IIb, or IIc:

IIa

IIb

IIc

X is an element chosen from O, S, Se, an N-alkyl group, or a C(alkyl)$_2$ group;

n is 1, 2 or 3;

$R^1$ comprises an alkyl group;

$R^2$, $R^3$, $R^4$, $R^5$, $R^6$, $R^7$, $R^8$, $R^9$, $R^{10}$, $R^{11}$, $R^{12}$, $R^{13}$, and $R^{14}$ are each independently chosen from hydrogen, an alkyl group, an aryl group, a heteroaryl group, a heterocycloaliphatic group, a hydroxyl group, an alkoxy group, an alkyl-substituted amine group, or a cyclic amine group, with the proviso that $R^1$ is not hydrogen or a hydroxyl group;

wherein two of $R^1$, $R^2$, $R^3$, $R^4$, $R^5$, $R^6$, $R^{10}$, $R^{11}$, $R^{12}$, and $R^{13}$ located ortho to each other can together comprise members of an aromatic ring, and at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, or $R^{14}$ represents a solubilizing, ionizable, or ionized substituent.

6. The method according to claim 5, wherein the polymethine fluorescence dye comprises a substituent chosen from a cyclodextrin, a sugar, $SO_3^-$, $PO_3^{2-}$, $COO^-$, or $NR_3^+$, wherein $NR_3^+$ is an amine group, the substituent optionally bonded to the polymethine fluorescence dye via a spacer group.

7. The method according to claim 1, wherein the polymethine fluorescence dye has a neutral charge, a single charge, or a double charge in a physiological solution.

8. The method according to claim 1, wherein the polymethine fluorescence dye comprises two or fewer solubilizing, ionizable, or ionized substituents.

9. The method according to claim 1, wherein the polymethine fluorescence dye is at least doubly charged.

10. The method according to claim 1, wherein the polymethine fluorescence dye comprises at least three solubilizing, ionizable, or ionized substituents.

11. The method according to claim 1, wherein the polymethine fluorescence dye is chosen from DY630, DY631, DY632, DY633, DY634, DY635, DY636, DY647, DY648, DY649, DY650, DY651, DY652, DY590, DY548, DY495, or DY405.

12. The method according to claim 1, wherein the method determines at least one organ function of a liver or kidney in a patient for monitoring the patient following a liver or kidney transplant.

13. The method according to claim 1, wherein the method determines at least one organ function of a liver or kidney in a patient for preventative examination.

14. The method according to claim 1, wherein the method determines at least one organ function of a liver or kidney in a patient for diagnosing the patient with sepsis or organ failure.

15. A kit for determining an organ function of a liver or kidney, the kit comprising:
at least one polymethine fluorescence dye without biological targeting moieties dissolved in a suitable solvent in a physiologically compatible form for administration, wherein the polymethine fluorescence dye has a fluorescence emission spectrum with a peak maximum of 820 nm or less when measured as a solution consisting of the polymethine fluorescence dye and ethanol;
at least one fluorescence detection device; and
at least one fluorescence data acquisition device.

16. The kit according to claim 15, wherein the polymethine fluorescence dye is in the form of an intravenously injectable solution.

17. The kit according to claim 15, wherein the polymethine fluorescence dye comprises an asymmetrical polymethine dye having a substituted omega-(benz[b]pyran-4-yliden)alk-1-enyl) unit of general structure 1:

wherein

Z is a substituted benzoxazole derivative, a benzothiazole derivative, a 2,3,3-trimethylindolenine derivative, a 2,3,3-trimethyl-4,5-benzo-3H-indolenine derivative, a 2-picoline derivative, a 4-picoline derivative, a lepidine derivative, a quinaldine derivative, or a 9-methylacridine derivative of general formula IIa, IIb, or IIc:

X is an element chosen from O, S, Se, an N-alkyl group, or a $C(alkyl)_2$ group;

n is 1, 2 or 3;

$R^1$ comprises an alkyl group;

$R^2$, $R^3$, $R^4$, $R^5$, $R^6$, $R^7$, $R^8$, $R^9$, $R^{10}$, $R^{11}$, $R^{12}$, $R^{13}$, and $R^{14}$ are each independently chosen from hydrogen, an alkyl group, an aryl group, a heteroaryl group, a heterocycloaliphatic group, a hydroxyl group, an alkoxy group, an alkyl-substituted amine group, or a cyclic amine group, with the proviso that $R^1$ is not hydrogen or a hydroxyl group;

wherein two of $R^1$, $R^2$, $R^3$, $R^4$, $R^5$, $R^6$, $R^{10}$, $R^{11}$, $R^{12}$, and $R^{13}$ located ortho to each other can together comprise members of an aromatic ring, and at least one of $R^1$, $R^2$, $R^3$, $R^4$, $R^5$, $R^6$, $R^7$, $R^8$, $R^9$, $R^{10}$, $R^{11}$, $R^{12}$, $R^{13}$ or $R^{14}$ represents a solubilizing, ionizable, or ionized substituent.

18. The kit according to claim 17, wherein the polymethine fluorescence dye comprises a substituent chosen from a cyclodextrin, a sugar, $SO_3^-$, $PO_3^{2-}$, $COO^-$, or $NR_3^+$, wherein $NR_3^+$ is an amine group, the substituent optionally bonded to the polymethine fluorescence dye via a spacer group.

19. The kit according to claim 15, wherein the polymethine fluorescence dye is chosen from DY630, DY631, DY632, DY633, DY634, DY635, DY636, DY647, DY648, DY649, DY650, DY651, DY652, DY590, DY548, DY495, or DY405.

20. The method of claim 1, wherein the polymethine fluorescence dye has a fluorescence emission spectrum with a peak maximum of 810 nm or less when measured as a solution consisting of the polymethine fluorescence dye and ethanol.

21. The method of claim 1, wherein the polymethine fluorescence dye has a fluorescence emission spectrum with a peak maximum of 800 nm or less when measured as a solution consisting of the polymethine fluorescence dye and ethanol.

22. A device for acquiring data with a marker in order to determine liver function or kidney function by measuring the in vivo fluorescence of one or more polymethine fluorescence dyes without biological targeting moieties dissolved in a suitable solvent, wherein the polymethine fluorescence dye has a fluorescence emission spectrum with a peak maximum of 820 nm or less when measured as a solution consisting of the polymethine fluorescence dye and ethanol.

23. The method of claim 5, wherein $R^5$ comprises a heteroaryl group, a heterocycloaliphatic group, a hydroxyl group, an alkoxy group, an alkyl-substituted amine group, or a cyclic amine group.

24. The method of claim 5, wherein $R^5$ comprises a heteroaryl group or a heterocycloaliphatic group, each comprising at least one oxygen heteroatom.

25. The method of claim 5, wherein $R^1$ comprises a group having a tertiary or quaternary carbon atom in the alpha position relative to the pyran ring to which it is a substituent.

26. The kit of claim 17, wherein $R^5$ comprises a heteroaryl group, a heterocycloaliphatic group, a hydroxyl group, an alkoxy group, an alkyl-substituted amine group, or a cyclic amine group.

27. The kit of claim 17, wherein $R^5$ comprises a heteroaryl group or a heterocycloaliphatic group, each comprising at least one oxygen heteroatom.

28. The kit of claim 17, wherein $R^1$ comprises a group having a tertiary or quaternary carbon atom in the alpha position relative to the pyran ring to which it is a substituent.

* * * * *